| (12) | United States Patent | (10) Patent No.: | US 6,891,033 B2 |
|---|---|---|---|
| | Martin et al. | (45) Date of Patent: | May 10, 2005 |

(54) LABELLING COMPOUNDS FOR THE SIMPLE SYNTHESIS OF 3'-[$^{18}$F]FLUORO-3'-DEOXYTHYMIDINE AND A METHOD FOR THE PRODUCTION THEREOF

(75) Inventors: Stefan Johannes Martin, Dossenheim (DE); Joseph Antonius Maria Eisenbarth, Ketsch (DE); Ulrike Wagner-Utermann, Heppenheim (DE); Michael Eisenhut, Heidelberg (DE); Walter Mier, Heidelberg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 10/470,817

(22) PCT Filed: Jan. 28, 2002

(86) PCT No.: PCT/EP02/00865

§ 371 (c)(1), (2), (4) Date: Jan. 13, 2004

(87) PCT Pub. No.: WO02/060913

PCT Pub. Date: Aug. 8, 2002

(65) Prior Publication Data

US 2004/0110720 A1 Jun. 10, 2004

(30) Foreign Application Priority Data

Jan. 31, 2001 (DE) .......................... 101 04 250

(51) Int. Cl.$^7$ ..................... C07H 19/06; A61K 31/7072
(52) U.S. Cl. ..................... 536/28.5; 536/28.54; 514/50
(58) Field of Search ............................. 536/28.5, 28.54; 514/50

(56) References Cited

U.S. PATENT DOCUMENTS 5,561,225 A 10/1996 Maddry et al.
2002/0102013 A1 8/2002 Gosselin et al.

FOREIGN PATENT DOCUMENTS

DE 694 07 419 T2 7/1998

OTHER PUBLICATIONS

European Journal of Nuclear Medicine, vol. 27 (8), p. 1220, 2000 (Abstract Only)).*
Sanghvi et al. (WO 01/73095 A2) (Abstract Sent).*
Schreiber et al. (Tetrahedron Letters (1988), 29(26), 3211–14) (Abstract Sent).*
International Search Report (PCT/EP02/00865)—3 pages.

Eisenbarth et al., "Precursors of [18F]FLT: Development of Simple Synthetic Pathways," Euopean Journal of Nuclear Medicine, vol. 27(8), pp. 1220, 2000 (XP–002199400).
Grierson, Jr. et al., "Developments in the Radiosynthesis of [F–18]FLT," Journal of Nuclear Medicine, vol. 39(5), pp. 22P, 1998 (XP–008003383).
Grierson, Jr. et al., "Radiosynthesis of 3'–Deoxy–3'[$^{18}$F] flourothymidine: [$^{18}$F]FLT for Imaging of Cellular Proliferation In Vivo," Nuclear Medicine & Biology, vol. 27, pp. 143–156, 2000 (XP–002199401).
Wilson et al., "Synthesis of 3'–flouro–3'–*Deoxythymidine* and Studies of its Fluorine–18 Radiolabeling, as a Tracer for the Noninvasive Monitoring of the Biodistribution of Drugs Against AIDS," J. Flourine Chem., vol. 55(3), pp. 283–289, 1991 (Chemical Abstract Only).

* cited by examiner

*Primary Examiner*—James O. Wilson
*Assistant Examiner*—Michael C. Henry
(74) *Attorney, Agent, or Firm*—Patterson, Thuente, Skaar & Christensen, P.A.

(57) ABSTRACT

The application relates to compounds that are suitable as labelable precursors for synthesis of 3'-[$^{18}$F]fluoro-3'-deoxythymidine and that have formula (1), in which
R denotes triphenylmethyl, triphenylmethyl substituted in the phenyl group, trialkylmethyl, triphenylsilyl, triphenylsilyl substituted in the phenyl group, or trialkylsilyl,
R' denotes $R^1$—$SO_2$, where $R^1$ is an unsubstituted or substituted $C_1$ to $C_5$ alkyl or an unsubstituted or substituted phenyl, and
R" denotes $C_2$ to $C_{10}$ alkyloxycarbonyl, with the exception of 3-N-Boc-1-(3-O-nosyl-5-O-trityl-2-deoxy-β-D-lyxofuranosy The application also relates to a method for preparation of these compounds and to the use of the same for synthesis of 3'-[$^{18}$F]fluoro-3'-deoxythymidine.

11 Claims, 1 Drawing Sheet

Fig. 1

LABELLING COMPOUNDS FOR THE SIMPLE SYNTHESIS OF 3'-[$^{18}$F]FLUORO-3'-DEOXYTHYMIDINE AND A METHOD FOR THE PRODUCTION THEREOF

The invention relates to compounds that are suitable as labelable precursors for synthesis of 3'-[$^{18}$F]fluoro-3'-deoxythymidine ([$^{18}$F]FLT), to methods for preparation of the same and to use of the same for synthesis of [$^{18}$F]FLT.

In nuclear medicine, positron emission tomography (PET) is used to investigate mechanisms of action of endogenous or exogenous substances (toxins, drugs) and to examine metabolic processes in the brain and other organs, especially in tumors. In fact, PET is frequently used precisely for tumor diagnosis. In this technique, biologically active compounds labeled with positron-emitting radionuclides are injected, and the emitted gamma radiation is measured in tomograms.

For this purpose there can be used, as the labeled compound, 3'-[$^{18}$F]fluoro-3'-deoxythymidine ([$^{18}$F]FLT)

which accumulates in rapidly dividing cells such as those present in tumors. In this way it is possible to locate tumors, for example, especially in the brain but also in the trunk, or to evaluate or optimize the response to a treatment regimen during the course of therapy.

Heretofore [$^{18}$F]FLT has been synthesized via several intermediate steps, in which there are used or formed highly toxic chemicals, which must then be completely separated prior to administration of the [$^{18}$F]FLT proliferation marker.

For example, J. R. Grierson and A. F. Shields (*Nucl. Med. Biol.*, 2000, 27, 143–156) describe a complex synthesis of labeling precursors for the preparation of [$^{18}$F]FLT, wherein highly toxic compounds such as phosgene are used in some steps. In these reactions there are used dimethoxybenzyl-N-protecting groups, which must be removed by oxidation with cerium(IV) ammonium nitrate. Because cerium compounds are toxic, however, they must be quantitatively separated in a reproducible precipitation reaction. These working steps must be performed manually. From the viewpoint of radiological protection, however, this should also be avoided, because the radiological burden and the danger of contamination of personnel must be kept as low as possible.

Machulla et al. (*J. Radioanal. Nucl. Chem.*, 2000, 243, 843–846) and Wodarski et al. (*J. Labelled Cpd. Radiopharm.* 2000, 43, 1211–1218) describe the synthesis of labeling precursors for preparation of [$^{18}$F]FLT. This synthesis, however, requires extreme reaction conditions such as reaction temperatures of around 160° C., and DMSO is used as solvent. As a result, the synthesis can be scaled up to commercially available synthesis modules to only a limited extent. Furthermore, DMSO is difficult to remove, because it is a high-boiling solvent.

The compound 3-N-Boc-1-(3-O-nosyl-5-O-trityl-2-deoxy-β-D-lyxofuranosyl)thymine for preparation of [$^{18}$F]FLT is described in Nuklearmedizin 2000; 38; 37–55, 8144; European Journal of Nuclear Medicine, 2000, Vol. 27, no. 8, pp. 889–1276, BP27-BP30 and 47$^{th}$ Annual Meeting of the Society of Nuclear Medicine, St. Louis, Mo., 3 to 7 Jun. 2000, Abstract 1123, 255P. Unfortunately, this compound [$^{18}$F]FLT is produced only in relatively low yields.

The object of the present invention is therefore to provide, for preparation of labelable compounds for the synthesis of [$^{18}$F]FLT, a means and a method that do not suffer from the known disadvantages of the prior art.

According to the invention, this is achieved by a compound characterized in that it has the structure of formula (1):

in which
R denotes triphenylmethyl, triphenylmethyl substituted in the phenyl group, trialkylmethyl, triphenylsilyl, triphenylsilyl substituted in the phenyl group, or trialkylsilyl,
R' denotes R$^1$—SO$_2$, where R' is an unsubstituted or substituted C$_1$ to C$_5$ alkyl or an unsubstituted or substituted phenyl, and
R" denotes C$_2$ to C$_{10}$ alkyloxycarbonyl,
with the exception of 3-N-Boc-1-(3-O-nosyl-5-O-trityl-2-deoxy-β-D-lyxofuranosyl)thymine.

In the inventive compound, the phenyl group in the triphenylmethyl or triphenylsilyl group can be substituted. The triphenylmethyl and triphenylsilyl groups each contain three phenyl groups, and so 1, 2 or 3 of the phenyl groups can be substituted. The substituents on the phenyl groups can be chosen independently of one another, although they can also be the same. A given phenyl group can contain 1 substituent or a plurality of substituents, which can be identical to or different from one another. The substituents can occupy the o-, m- and/or p-position relative to the methyl carbon or to the Si atom. As substituents there can be used in particular groups that exert a +M effect and do not react with functional groups of the starting materials and products used for preparation and further processing of the inventive compound.

Besides the methyl group, ethyl, methoxy and ethoxy are preferred substituents on the phenyl group, since they have a particularly favorable +M effect.

In a preferred embodiment of the inventive compound, R denotes 4,4'-dimethoxytriphenylmethyl, which for the present case is a particularly good leaving group, which can be removed in particularly gentle and simple manner, especially under mild conditions (pH, low temperatures). In addition, it can be easily synthesized and introduced into the inventive compound. The 4,4'-dimethoxytriphenylmethyl group can be selectively introduced in high yield at the OH group in 5'-position under mild conditions, such as room temperature. Furthermore, inventive compounds containing dimethoxytriphenylmethyl groups lead to [$^{18}$F]FLT in high yields.

In the inventive compound, the group R can be a trialkylmethyl or trialkylsilyl group. The alkyl groups can be the same or different. Preferably they are chosen from among the $C_1$ to $C_5$ alkyl groups. In a favorable embodiment, at least one of the three alkyl groups is a sterically demanding alkyl group, such as a branched alkyl group, to ensure that no unwanted reaction with the OH group in 3'-position takes place during introduction of the group R into the inventive compound. Examples of suitable sterically demanding alkyl groups are tert-butyl and isopropyl. The remaining alkyl groups of the trialkyl group can be sterically less demanding $C_1$ to $C_5$ alkyl groups, especially methyl. Examples of R are tert-butyldimethylsilyl and triisopropylsilyl.

According to the foregoing formula (1), R' denotes $R^1$—$SO_2$, where $R^1$ can be an unsubstituted or substituted $C_1$ to $C_5$ alkyl. An example of an unsubstituted $C_1$ to $C_5$ alkyl group is methyl, in which case $R^1$—$SO_2$ denotes methanesulfonyl. This is preferred, since mesylation, or in other words the reaction with which it is introduced into the inventive compound, takes place rapidly and the product is obtained in high yields. The substituent on the substituted $C_1$ to $C_5$ alkyl group is preferably an electron-attracting group, so that the group R' represents a good leaving group. Examples of electron-attracting groups are, besides $NO_2$, halogens such as F, Cl, Br and I. Of those, fluorine is particularly suitable because of its favorable electron-attracting nature. In the substituted $C_1$ to $C_5$ alkyl group, at least 1 H atom and as many as all H atoms of the alkyl group can be replaced by an electron-attracting substituent. A particularly preferred representative of the substituted $C_1$ to $C_5$ alkyl group is $CF_3$, in which case $R_1$—$SO_2$ denotes trifluoromethanesulfonyl.

As already explained hereinabove, the group $R^1$ can be an unsubstituted or substituted phenyl group. It can contain 1 or more substituents, which can be the same or different. The substituents can occupy the o-, m- or p-position relative to the $SO_2$ group. Examples of suitable substituents are $C_1$ to $C_5$ alkyl groups, such as methyl, or electron-attracting substituents, especially halogens such as F, Cl, Br and I, and also the $NO_2$ group.

Preferred $R^1$—$SO_2$ groups are 4-nitrophenylsulfonyl or p-toluenesulfonyl.

Particularly favorable representatives of the $C_2$ to $C_{10}$ alkoxycarbonyl group indicated in formula (1) are tert-butoxycarbonyl and neopentoxycarbonyl. These are particularly suitable because, when they are removed by acid hydrolysis, they produce $CO_2$ and an alcohol, which can be separated efficiently, almost completely and easily from the reaction mixture.

Preferred inventive compounds are 3-N-Boc-1-(3-O-tosyl-5-O-trityl-2-deoxy-β-D-lyxofuranosyl)thymine, 3-N-Boc-1-(3-O-mesyl-5-O-trityl-2-deoxy-β-D-lyxofuranosyl) thymine, 3-N-Boc-1-(5-O-(4,4'-dimethoxytrityl)-3-O-nosyl-2-deoxy-β-D-lyxofuranosyl) thymine, 3-N-Boc-1-(5-O-(4,4'-dimethoxytrityl)-3-O-tosyl-2-deoxy-β-D-lyxofuranosyl) thymine and 3-N-Boc-1-(5-O-(4,4'-dimethoxytrityl)-3-O-mesyl-2-deoxy-β-D-lyxofuranosyl) thymine.

Surprisingly, it has now been found that the compound [$^{18}$F]FLT used in positron-emission tomography can be prepared simply and rapidly by starting from the inventive compounds. It was further completely surprising that the inventive compounds can be prepared simply and rapidly in good yields and high purity under mild conditions.

Further subject matter of the present invention is a method for preparation of the inventive compound of formula (1), wherein a compound of formula (2)

in which R and R' are as defined hereinabove, is reacted with pyrocarbonic acid di-$C_2$-$C_{10}$ alkyl esters.

The reaction of such an ester, such as pyrocarbonic acid di-tert-butyl ester ($Boc_2O$), with an N atom in a molecule is known to the person skilled in the art, who is familiar with reaction conditions, chemicals and apparatus necessary for this purpose. For example, this reaction can be performed under inert gas and at room temperature. As the solvent there can be used anhydrous pyridine, for example. Isolation and purification of the desired product, or in other words the inventive compound, can be achieved in standard manner. As an example, the solvent can be removed under reduced pressure, and the raw product can be purified chromatographically, for example on silica gel.

The compound of formula (2) can be prepared preferably by reacting the compound of formula (3)

with $R^1$—$SO_2Hal$, where $R^1$ is as defined hereinabove and Hal denotes a halogen, especially chlorine, whereby the substituent R' is introduced. Examples of $R^1$—$SO_2Hal$ are methanesulfonyl chloride, 4-nitrophenylsulfonyl chloride, p-toluenesulfonyl chloride and trifluoromethanesulfonic acid chloride. This reaction can be performed favorably at room temperature. Anhydrous pyridine or a mixture of triethylamine and dichloromethane can be used as solvent. The compound of formula (3) can be placed in the solvent and the compound of formula $R^1$—$SO_2Hal$ added. Isolation and purification of the raw product of formula (2) obtained by the foregoing reaction can be achieved, for example, by removing the solvent under reduced pressure followed by chromatographic purification, for example on silica gel.

The compound of formula (3)—if it is not commercially available—can be prepared from thymidine by introduction of the protecting group R and inversion. These reactions are known to the person skilled in the art, who is familiar with reaction conditions, chemicals and apparatus necessary for the purpose.

To introduce the protecting group R into the thymidine molecule, the thymidine can be dissolved in pyridine, for example, and reacted under inert gas with a compound of the R-Hal type, wherein R is as defined hereinabove and Hal denotes a halogen, especially chlorine. Examples of R-Hal are triphenylmethyl chloride and 4,4'-dimethoxytriphenylmethyl chloride.

One synthesis pathway for the inventive compound, starting from thymidine, is illustrated in summary form below, wherein the inventive method represents the last step.

Therein the groups R, R' and R" have the foregoing meanings.

If products shown as intermediates in the foregoing synthesis scheme are commercially available, such as the compound of formula (3), in which R denotes triphenylmethyl, naturally the synthesis of the inventive compound can be achieved starting from the commercial compounds.

The inventive method exhibits several advantages. For example, commercial reagents that can be obtained quickly and inexpensively are used as starting materials and solvents. Furthermore, universally standard laboratory techniques are used, such as In further aspects, the invention relates to a method for synthesizing 3'-[$^{18}$F]fluoro-3'-deoxythymidine. the method comprising reacting a compound with a formula:

(1)

in which

R denotes triphenylmethyl, triphenylmethyl substituted in the phenyl group, trialkylmethyl, triphenylsilyl, triphenylsilyl substituted in the phenyl group, or trialkylsilyl, R' denotes $R^1$—$SO_2$, where $R^1$ is an unsubstituted or substituted $C_1$ to $C_5$ alkyl or an unsubstituted or substituted phenyl, and R" denotes $C_2$ to $C_{10}$ alkyloxycarbonyl, with the exception of 3-N-Boc-1-(3-O-nosyl-5-O-trityl-2-deoxy-β-D-lyxofuranosyl)thymine, with a composition to substitute the OR' group by $^{18}$F. The method can further comprise removing the protecting groups R" and R. reaction at room temperature, performance of the reactions with standard stirrers, use of inert gas and chromatographic methods for isolation and purification of products. The reaction temperature in the inventive method is low, and so complex apparatus is not necessary for heating. The solvents used in the inventive method are generally low-boiling and thus can be easily separated. The inventive method can be automated, and so it is favorable from the viewpoint of radiological protection, since the radiation burden and contamination of personnel are kept as low as possible. Starting from the inventive compounds prepared with the inventive method, the [$^{18}$F]FLT used in positron-emission tomography can be synthesized simply and rapidly in high yield and high purity.

Further subject matter of the present invention is the use of the inventive compound for synthesis of [$^{18}$F]FLT. For this purpose, the OR' group is preferably substituted by $^{18}$F. The protecting groups R" and R can then be removed, preferably by acid hydrolysis.

During the labeling reaction, the inventive compound containing [$^{18}$F]fluoride can be reacted in an organic solvent, especially acetonitrile, in the presence of a base such as potassium carbonate and of a macrocyclic neutral ligand such as Kryptofix® 222 of Merck, to obtain [$^{18}$F]FLT protected by R and R". The [$^{18}$F]FLT target compound can be hydrolyzed with dilute hydrochloric acid. Since the pattern of protecting groups in the inventive compound permits simple acid hydrolysis of the [$^{18}$F]-labeled intermediate by means of dilute hydrochloric acid in homogeneous solution, only nontoxic sodium chloride (common salt) is obtained after neutralization. This salt can be separated in simple manner by means of HPLC. The raw [$^{18}$F]FLT product can be purified chromatographically, for example with an aluminum oxide cartridge and/or by means of HPLC (for example, mobile phase: H$_2$O:ethanol=92.5:7.5, isocratic; column: Phenomenex LUNA 5μ250×4.6 mm).

Compared with the acyl protecting group, for example, the use of Boc as the protecting group in the inventive compound, which can be used for synthesis of [$^{18}$F]FLT, has the advantage that there is no loss of yield during the [$^{18}$F]FLT synthesis or that the loss of yield, if it occurs at all, is not significant.

By means of the inventive use, or in other words the use of the inventive compound for synthesis of the [$^{18}$F]FLT proliferation marker, it is possible to synthesize this proliferation marker in surprisingly simple and rapid manner under mild conditions in good yields and high purity. This synthesis method can be automated, or in other words a system can be designed with which this method can be performed automatically. This is preferred from the viewpoint of radiological protection, since the radiation burden and contamination of personnel are low in a fully automatic process. Since the proliferation marker is obtainable in high yield when synthesized starting from the inventive compound, it can be administered to the patient either immediately or without further complex purification steps, without causing adverse effects in the patient as a result of possible impurities. By virtue of the high yield in which the proliferation marker can be obtained, sufficient quantities of marker for examination of several patients can be obtained in one radiosynthesis.

Figure 1:
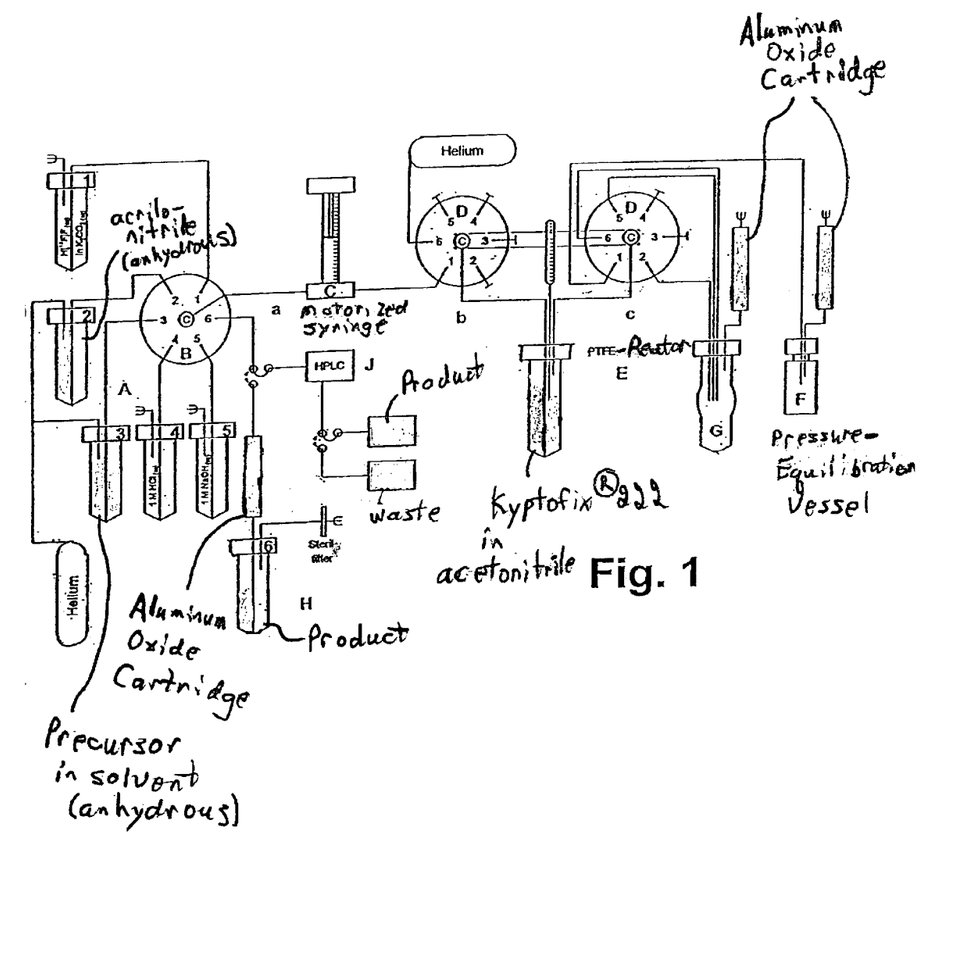

The invention will be explained in more detail by the following examples, in which connection FIG. 1 shows a system such as used in Example 6 for synthesis of [$^{18}$F]FLT.

EXAMPLE 1

Synthesis of the Compound 3-N-Boc-1-(3-O-mesyl-5-O-trityl-2-deoxy-β-D-lyxofuranosyl)thymine
1. Synthesis of 5'-O-tritylthymidine

| Starting mixture: | | |
|---|---|---|
| 5.15 g | (21.26 mmol) | thymidine |
| 7.02 g | (25.18 mmol) | triphenylmethyl chloride (trityl chloride) |
| 100 ml | | pyridine (anhydrous) |

Procedure: In a 250-ml three-necked flask, trityl chloride is placed in anhydrous pyridine under inert gas and stirring, and the thymidine is added. After 30 minutes of heating to t=110° C. (heating-bath temperature), the yellowish reaction solution is allowed to cool and is then decanted slowly into 1.5 l of vigorously stirred ice water. After 30 minutes of stirring, the milky-white suspension is suction-filtered, the filter cake is dissolved in acetone and the solution is filtered once again. The solvent is removed in the rotary evaporator and the solid is dried for 16 hours in high vacuum. The product, 5'-O-tritylthymidine, is obtained by recrystallization two times from a benzene-acetone mixture.

| Yield: | 8.60 g | (17.75 mmol) | 83.5% of theoretical |
|---|---|---|---|
| Properties: | fibrous, faintly yellow solid; | | |
| | m.p. = 133.0 to 136.9° C.; | | |
| | R$_f$ = 0.29 (V(MeOH):V(CH$_2$Cl$_2$) = 1:19) | | |

2. Synthesis of 1-(5-O-trityl-2-deoxy-β-D-lyxofuranosyl)thymine

| Starting mixture: | | |
|---|---|---|
| 0.96 g | (1.98 mmol) | 5'-O-tritylthymidine |
| 0.34 g | (2.97 mmol, 0.23 ml) | methanesulfonyl chloride (mesyl chloride) |
| 0.50 g | (4.94 mmol, 0.68 ml) | triethylamine |
| 15 ml | | tetrahydrofuran (dried over sodium, freshly distilled) |
| 5 ml | | ethanol |
| 5 ml | | 1 M NaOH (aq) |
| 3.4 ml | | 10 M NaOH (aq) |

Procedure: In a 50-ml one-necked flask with lateral stopcock, 5'-O-tritylthymidine and triethylamine are placed in THF at t=0° C. under inert gas and stirring. Mesyl chloride is added dropwise from a syringe. The initially colorless solution becomes faintly yellow and cloudy. The reaction solution is allowed to warm up to room temperature within 30 minutes under stirring. Instead of the spot corresponding to starting material (R$_f$=0.29), a spot corresponding to the mesylated compound (R$_f$=0.45) is evident in TLC (V(MeOH):V(CH$_2$Cl$_2$)=1:19). At this point, 5 ml each of water, ethanol and 1 M sodium hydroxide solution are added to the reaction solution, which is stirred for 1 hour under reflux. In the TLC control test (V(MeOH):(VCH$_2$Cl$_2$)=1:19), exclusively the spot corresponding to the anhydro compound (R$_f$=0.15) is visible. Thereafter 3.4 ml of 10 M sodium hydroxide solution is added and the mixture stirred for 30 minutes under reflux. Two phases can form during this step. Instead of a spot corresponding to the anhydro compound (R$_f$=0.15), the product spot (R$_f$=0.33) is now evident on the TLC plate (V(MeOH):V(CH$_2$Cl$_2$)=1:19). The reaction solution is mixed with about 6 g of silica gel 60, and the solvent mixture is distilled off in the rotary evaporator. Subsequent column chromatography under flash conditions (silica gel 60; Ø=2.9 cm; h=32 cm; V(MeOH):V(CH$_2$Cl$_2$)=1:19+0.1% of triethylamine; 8.5 ml/min) yields the product, 1-(5-O-trityl-2-deoxy-β-D-lyxofuranosyl)thymine.

In the case of starting mixtures from which product quantities of m≧2.5 g can be expected, the following work-up procedure can be used instead of column chromatography:

The solvent mixture is concentrated in the rotary evaporator until a white flocculent solid is precipitated. The remaining aqueous phase is diluted with 400 ml of water and extracted three times with 400 ml portions of ethyl acetate. The united organic phases are dried with magnesium sulfate, and the ethyl acetate is removed by means of the rotary evaporator at first and then by high vacuum for several hours, whereupon the product is obtained in sufficient purity. Complete separation of the sodium hydroxide can be confirmed by measurement of the pH of a solution of the product in acetone/water (V(acetone):V(H$_2$O)=1:1).

| Yield: | 0.51 g | (1.05 mmol) | 53.0% of theoretical |
|---|---|---|---|
| Properties: | colorless, amorphous solid; | | |
| | m.p. = 246 to 248° C.; | | |
| | R$_f$ = 0.33 (V(MeOH):V(CH$_2$Cl$_2$) = 1:19) | | |

3. Synthesis of 1-(3-O-mesyl-5-O-trityl-2-deoxy-β-D-lyxofuranosyl)thymine

| Starting mixture: | | |
|---|---|---|
| 0.50 g | (1.03 mmol) | 1-(5-O-trityl-2-deoxy-β-D-lyxofuranosyl)thymine |
| 0.59 g | (5.15 mmol, 0.40 ml) | methanesulfonyl chloride (mesyl chloride) |
| 0.53 g | (5.24 mmol, 0.73 ml) | triethylamine |
| 20 ml | | dichloromethane (anhydrous) |

Procedure: In a 25-ml one-necked flask with lateral stopcock, the 1-(5-O-trityl-2-deoxy-β-D-lyxofuranosyl)thymine is placed in anhydrous dichloromethane at room temperature under inert gas and stirring, and then triethylamine is added. Mesyl chloride is added dropwise from a syringe. Within 30 minutes, the color of the reaction solution changes from colorless to yellow. In the subsequent TLC control test (V(MeOH):V(CH$_2$Cl$_2$)=1:19), the spot corresponding to the starting material ($R_f$=0.33) is no longer visible. About 3 g of silica gel is added to the reaction solution, and the solvent is removed in the rotary evaporator. The product is isolated by flash column chromatography (silica gel 60; Ø=2.9 cm; h=30 cm; V(MeOH):V(CH$_2$Cl$_2$)= 1:19+0.1% of triethylamine).

| Yield: | 0.51 g | (0.91 mmol) | 88.3% of theoretical |
|---|---|---|---|
| Properties: | colorless, amorphous solid; | | |
| | m.p. = 99.8 to 102.0° C.; | | |
| | $R_f$ = 0.41 V(MeOH):V(CH$_2$Cl$_2$) = 1:19 | | |

4. Synthesis of the Product Compound

| Starting mixture: | | |
|---|---|---|
| 0.53 g | (0.94 mmol) | 1-(3-O-mesyl-5-O-trityl-2-deoxy-β-D-lyxofuranosyl)thymine |
| 0.62 g | (2.84 mmol, 0.65 ml) | pyrocarbonic acid di-tert-butyl ester (Boc$_2$O) |
| 10 ml | | pyridine (anhydrous) |

Procedure: In a 25-ml one-necked flask with lateral stopcock, a solution of 1-(3-O-mesyl-5-O-trityl-2-deoxy-β-D-lyxofuranosyl)thymine in anhydrous pyridine is prepared under inert gas, and Boc$_2$O is added dropwise at room temperature with stirring. After 2.5 days, the TLC control test (V(Et$_2$O)=100) shows the reaction to be almost complete, since only a faint spot corresponding to the starting material ($R_f$=0.10) is still evident. About 3 g of silica gel 60 is added to the orange-brown reaction solution, and the solvent is removed by using a rotary evaporator. For complete removal of the pyridine, the raw product is dried for 16 hours in high vacuum. The title product, or in other words the inventive compound, is purified by means of flash column chromatography (silica gel 60; Ø=2.3 cm; h=28 cm; V(Et$_2$O)=100+0.1% of triethylamine; 6.3 m/min).

| Yield: | 0.42 g | (0.63 mmol) | 67.0% of theoretical |
|---|---|---|---|
| Properties: | colorless, amorphous solid; | | |
| | m.p. = 157.1 to 158.7° C. (decomposition); | | |
| | $R_f$ = 0.50 (V(Et$_2$O) = 100) | | |

EXAMPLE 2

Synthesis of the Compound 3-N-Boc-1-(3-O-tosyl-5-O-trityl-2-deoxy-β-D-lyxofuranosyl)thymine

1. Synthesis of 1-(3-O-tosyl-5-O-trityl-2-deoxy-β-D-lyxofuranosyl)thymine

| Starting mixture: | | |
|---|---|---|
| 0.88 g | (1.82 mmol) | 1-(5-O-trityl-2-deoxy-β-D-lyxofuranosyl)thymine, prepared according to Example 1 |
| 1.06 g | (5.56 mmol) | p-toluenesulfonyl chloride (tosyl chloride) |
| 15 ml | | pyridine (anhydrous) |

Procedure: In a 25-ml one-necked flask with lateral stopcock, 1-(5-O-trityl-2-deoxy-β-D-lyxofuranosyl)thymine is placed in anhydrous pyridine at room temperature under inert gas and stirring, and the tosyl chloride is added. The reaction solution, which becomes pink after 2 hours and orange-colored later, is stirred for 60 hours. In the TLC control test (V(MeOH):V(CH$_2$Cl$_2$)=1:19), a distinct but not complete reaction is evident on the basis of the spot corresponding to the starting material ($R_f$=0.33). Thereafter about 3 g of silica gel 60 is added to the reaction solution, and the solvent is removed by means of the rotary evaporator at first and then by high vacuum for 16 hours. The product is isolated by means of flash column chromatography (silica gel 60; Ø=4.9 cm; h=30 cm; V(MeOH):V(CH$_2$Cl$_2$)=1:19+ 0.1% of triethylamine; 5 ml/min).

| Yield: | 0.28 g | (0.44 mmol) | 24.2% of theoretical |
|---|---|---|---|
| Properties: | colorless, amorphous solid; | | |
| | m.p. = 100.5 to 109.0° C.; | | |
| | $R_f$ = 0.52 (V(MeOH):V(CH$_2$Cl$_2$) = 1:19) | | |

2. Synthesis of the Product Compound

| Starting mixture: | | |
|---|---|---|
| 0.47 g | (0.74 mmol) | 1-(3-O-tosyl-5-O-trityl-2-deoxy-β-D-lyxofuranosyl)thymine |
| 0.48 mg | (2.20 mmol, 0.51 ml) | pyrocarbonic acid di-tert-butyl ester (Boc$_2$O) |
| 10 ml | | pyridine (anhydrous) |

Procedure: In a 25-ml one-necked flask with gas connection, a solution of 1-(3-O-tosyl-5-O-trityl-2-deoxy-β-D-lyxofuranosyl)thymine in anhydrous pyridine is introduced at room temperature under inert gas and stirring, and Boc$_2$O is added dropwise. After 3.5 days of stirring of the reaction solution, which is pale yellow at first and orange-colored later, a spot of low intensity corresponding to the starting material ($R_f$=0.30) is still evident in TLC (V(Et$_2$O)=100). About 3 g of silica gel 60 is added, and the solvent is removed by means of the rotary evaporator at first and then by high vacuum for 16 hours. The product is obtained by flash chromatography (silica gel 60; Ø=4.9 cm; h=32 cm;

V(Et$_2$O)=100+0.1% of triethylamine), and the inventive compound crystallizes out during removal of the eluent.

| Yield: | 0.32 g | (0.43 mmol) | 58.1% of theoretical |
|---|---|---|---|
| Properties: | colorless, amorphous solid; | | |
| | m.p. = 174.3 to 175.4° C. (decomposition); | | |
| | R$_f$ = 0.68 (V(Et$_2$O) = 100) | | |

EXAMPLE 3

Synthesis of the Compound 3-N-Boc-1-(5-O-(4,4'-dimethoxytrityl)-3-O-mesyl-2-deoxy-β-D-lyxofuranos 1. Synthesis of 5'-O-(4,4'-dimethoxytrityl)thymidine

| Starting mixture: | | |
|---|---|---|
| 5.12 g | (21.14 mmol) | thymidine |
| 8.56 g | (25.26 mmol) | 4,4-dimethoxytriphenylmethyl chloride (dimethoxytrityl chloride) |
| 100 ml | | pyridine (anhydrous) |

Procedure: In a 250-ml three-necked flask, thymidine and dimethoxytrityl chloride in anhydrous pyridine are introduced in succession under inert gas and stirred for 2 hours at room temperature. The TLC control test of the reaction (V(MeOH):V(CH$_2$Cl$_2$)=1:19) shows the 5'-O-protected compound (R$_f$=0.26) to be the main product. It also contains one faint spot each for the starting material (R$_f$=0.00) and the doubly protected byproduct, 3',5'-bis-O-(4,4'-dimethoxytrityl)thymidine (R$_f$=0.71). The reaction solution is then decanted slowly into 1.5 l of vigorously stirred ice water. After 30 minutes of stirring, the yellow suspension is suction-filtered, and the residual moisture is removed from the solid in the rotary evaporator by azeotropic distillation two times with ethanol. Alternatively, the raw product is recrystallized from a benzene-acetone mixture or is purified by means of column chromatography (silica gel 60; Ø=6 cm; h=45 cm; V(MeOH):V(CH$_2$Cl$_2$)=1:19+0.1% of triethylamine; absorbed on about 20 g of silica gel 60). After drying in high vacuum, it yields the product, 5'-O-(4,4'-dimethoxytrityl)thymidine.

| Yield: | 10.54 g | (19.35 mmol) | 91.5% of theoretical |
|---|---|---|---|
| Properties: | beige-colored, amorphous solid; | | |
| | m.p. = 114 to 116° C. (sublimation); | | |
| | R$_f$ = 0.23 (V(MeOH):V(CH$_2$Cl$_2$) = 1:19) | | |

2. Synthesis of 1-(5-O-(4,4'-dimethoxytrityl)-2-deoxy-β-D-lyxofuranosyl)thymine

| Starting mixture: | | |
|---|---|---|
| 10.04 g | (18.44 mmol) | 5'-O-(4,4-dimethoxytrityl)thymidine |
| 3.26 g | (28.46 mmol, 2.2 ml) | methanesulfonyl chloride (mesyl chloride) |
| 4.82 g | (47.63 mmol, 6.6 ml) | triethylamine |
| 160 ml | | tetrahydrofuran (dried over sodium, freshly distilled) |
| 53 ml | | ethanol |
| 53 ml | | 1 M NaOH (aq) |
| 37 ml | | 10 M NaOH (aq) |

Procedure: In a 500-ml one-necked flask with gas connection, 5'-O-(4,4'-dimethoxytrityl)thymidine and triethylamine are dissolved in anhydrous tetrahydrofuran under inert gas and stirring, and are cooled to a temperature of between t≈−8 and 0° C. (ice/ethanol). Mesyl chloride is slowly added dropwise to the reaction solution, which is then stirred for 30 minutes. Instead of the spot corresponding to starting material (R$_f$=0.26), the spot corresponding to the mesylated compound (R$_f$=0.39) is evident on the TLC plate (V(MeOH):V(CH$_2$Cl$_2$)=1:19). The ice bath is removed and 53 ml each of water, ethanol and 1 M sodium hydroxide solution are added to the cloudy, yellow reaction solution, which is stirred for 90 minutes under reflux. In TLC (V(MeOH):V(CH$_2$Cl$_2$)=1:19), exclusively the spot corresponding to the anhydro compound (R$_f$=0.20) is visible. Thereafter 37 ml of 10 M sodium hydroxide solution is added, whereupon the intense-yellow solution forms two phases. After 45 minutes of stirring at a heating-bath temperature of t≈85 to 90° C., the reaction is left at room temperature for 16 hours in order to go to completion. The TLC control test (V(MeOH):V(CH$_2$Cl$_2$)=1:19) shows the formation of the desired product (R$_f$=0.31). The THF is largely removed from the reaction mixture in the rotary evaporator, then the remaining aqueous phase is diluted to 400 ml with water and extracted three times with 400-ml portions of ethyl acetate. The united organic phases are dried over magnesium sulfate, and the solvent is removed by means of the rotary evaporator at first and then by means of high vacuum, whereupon the product is obtained in sufficient purity. Complete separation of the sodium hydroxide can be confirmed by measurement of the pH of a solution of the product in acetone/water (V(acetone):V(H$_2$O))=1:1).

| Yield: | 9.32 g | (17.11 mmol) | 92.8% of theoretical |
|---|---|---|---|
| Properties: | colorless, amorphous solid; | | |
| | R$_f$ = 0.31 (VMeOH:VCH$_2$Cl$_2$ = 1:19) | | |

3. Synthesis of 1-(5-O-(4,4'-dimethoxytrityl)-3-O-mesyl-2-deoxy-β-D-lyxofuranosyl)thymine

| Starting mixture: | | |
|---|---|---|
| 1.97 g | (3.62 mmol) | 1-(5-O-(4,4'-dimethoxytrityl)-2-deoxy-β-D-lyxofuranosyl)thymine |
| 0.83 g | (7.25 mmol, 0.56 ml) | methanesulfonyl chloride (mesyl chloride) |
| 1.10 g | (10.82 mmol, 1.51 ml) | triethylamine |
| 25 ml | | dichloromethane (anhydrous) |

Procedure: In a 50-ml one-necked flask with gas connection, the 1-(5-O-(4,4'-dimethoxytrityl)-2-deoxy-β-D-lyxofuranosyl)thymine and the triethylamine are placed in anhydrous dichloromethane under inert gas and stirring, and the mesyl chloride is slowly added dropwise at t=0° C. After 45 minutes of stirring, the yellowish cloudy reaction solution has reached room temperature. In the subsequent TLC control test (V(MeOH):V(CH$_2$Cl$_2$)=1:19), the spot corresponding to the starting material (R$_f$=0.33) is no longer visible. About 4 g of silica gel 60, and the solvent is removed in the rotary evaporator. The product is isolated by means of column chromatography (silica gel 60; Ø=4.5 cm; h=25 cm; V(MeOH):V(CH$_2$Cl$_2$)=1:19+0.1% of triethylamine).

| Yield: | 1.83 g | (2.94 mmol) | 81.2% of theoretical |
|---|---|---|---|
| Properties: | colorless, amorphous solid; | | |
| | R$_f$ = 0.43 (VMeOH):V(CH$_2$Cl$_2$) = 1:19) | | |

4. Synthesis of the Product Compound

| Starting mixture: | | |
|---|---|---|
| 1.65 g | (2.65 mmol) | 1-(5-O-(4,4'-dimethoxytrityl)-3-O-mesyl-2-deoxy-β-D-lyxofuranosyl)thymine |
| 3.52 g | (16.13 mmol, 3.7 ml) | pyrocarbonic acid di-tert-butyl ester (Boc$_2$O) |
| 30 ml | | pyridine (anhydrous) |

Procedure: In a 100-ml one-necked flask with gas connection, the 1-(5-O-(4,4'-dimethoxytrityl)-3-O-mesyl-2-deoxy-β-D-lyxofuranosyl)thymine is placed in anhydrous pyridine under inert gas, Boc$_2$O is added and the reaction solution is stirred at room temperature. After several TLC control tests (V(Et$_2$O)=100) within 2 days, no further reaction is perceptible. Besides the spot corresponding to the starting material (R$_f$=0.07), a spot (R$_f$=0.44) is observed that represents overlapping of an unidentified byproduct (R$_f$=0.93, V(MeOH):V(CH$_2$Cl$_2$)=1:19) with the desired product (R$_f$=0.84; V(MeOH):V(CH$_2$Cl$_2$)=1:19, Merck® TLC plates). About 6 g of silica gel 60 is added to the dark-brown reaction solution, and the solvent is removed by means of the rotary evaporator at first and then by means of high vacuum for 16 hours. Column chromatography (silica gel 60; Ø=5 cm; h=30 cm; V(Et$_2$O)=100+0.1% of triethylamine) yields the title product as the second fraction.

| Yield: | 0.32 g | (0.44 mmol) | 16.6% of theoretical |
|---|---|---|---|
| Properties: | yellow, amorphous solid; | | |
| | m.p. = 79.0 to 85.5° C. (decomposition); | | |
| | R$_f$ = 0.44 (V(Et$_2$O) = 100) | | |

EXAMPLE 4

Synthesis of the Compound 3-N-Boc-1-(5-O-(4,4'-dimethoxytrityl)-3-O-tosyl-2-deoxy-β-D-lyxofuranos 1. Synthesis of 1-(5-O-(4,4'-dimethoxytrityl)-3-O-tosyl-2-deoxy-β-D-lyxofuranosyl)thymine

| Starting mixture: | | |
|---|---|---|
| 2.00 g | (3.67 mmol) | 1-(5-O-(4,4'-dimethoxytrityl)-2-deoxy-β-D-lyxofuranosyl)thymine, prepared according to Example 3 |
| 3.50 g | (18.36 mmol) | p-toluenesulfonyl chloride (tosyl chloride) |
| 30 ml | | pyridine (anhydrous) |

Procedure: In a 100-ml three-necked flask with gas connection, 1-(5-O-(4,4'-dimethoxytrityl)-2-deoxy-β-D-lyxofuranosyl)thymine and tosyl chloride are dissolved in succession in anhydrous pyridine at room temperature under inert gas and stirring, then are stirred for 7 days. In the TLC control test (V(MeOH):V(CH$_2$Cl$_2$)=1:19), the course of the reaction can be evaluated to only a limited extent, since the spot corresponding to the starting material (R$_f$=0.31) is overlapped by the spots corresponding to tosyl chloride and to pyridine. Beyond the product spot (R$_f$=0.50), several byproduct spots are evident. About 5 g of silica gel 60 is added to the orange-red reaction solution, and the solvent is removed by means of the rotary evaporator at first and then by high vacuum for 16 hours. The title compound is purified by column chromatography (silica gel 60; Ø=4.5 cm; h=33 cm; V(MeOH):V(CH$_2$Cl$_2$)=1:19+0.1% of triethylamine).

| Yield: | 0.83 g | (1.19 mmol) | 32.4% of theoretical |
|---|---|---|---|
| Properties: | beige-colored, amorphous solid; | | |
| | R$_f$ = 0.50 (V(MeOH):V(CH$_2$Cl$_2$) = 1:19) | | |

2. Synthesis of the Product Compound

| Starting mixture: | | |
|---|---|---|
| 0.70 g | (1.00 mmol) | 1-(5-O-(4,4'-dimethoxytrityl)-3-O-tosyl-2-deoxy-β-D-lyxofuranosyl)thymine |
| 0.67 mg | (3.07 mmol, 0.71 ml) | pyrocarbonic acid di-tert-butyl ester (Boc$_2$O) |
| 25 ml | | pyridine (anhydrous) |

Procedure: In a 50-ml one-necked flask with lateral stopcock, 1-(5-O-(4,4'-dimethoxytrityl)-3-O-tosyl-2-deoxy-β-D-lyxofuranosyl)thymine is dissolved in anhydrous pyridine at room temperature under inert gas and stirring, Boc$_2$O is added and the mixture is stirred for 6 days. In TLC (V(Et$_2$O)=100%), both the starting-material sport (R$_f$=0.21) and the product spot (R$_f$=0.67) are visible. About 5 g of silica gel 60 is added to the brown reaction solution, and the pyridine is removed by means of the rotary evaporator at first and then by high vacuum for 16 hours. Column chromatography (silica gel 60; Ø=4.0 cm; h=30 cm; V(Et$_2$O)=100+0.1% of triethylamine) yields the product.

| Yield: | 0.50 g | (0.63 mmol) | 63.0% of theoretical |
|---|---|---|---|
| Properties: | pale-yellow, amorphous solid; m.p. = 87.0 to 93.0° C. | | |
| | R$_f$ = 0.67 (V(Et$_2$O) = 100%) | | |

EXAMPLE 5

Synthesis of the Compound 3-N-Boc-1-(5-O-(4,4'-dimethoxytrityl)-3-O-nosyl-2-deoxy-β-D-lyxofuranos 1. Synthesis of 1-(3-O-nosyl-5-O-(4,4'-dimethoxytrityl)-2-deoxy-β-D-lyxofuranosyl)thymine

| Starting mixture: | | |
|---|---|---|
| 0.58 g | (1.07 mmol) | 1-(5-O-(4,4'-dimethoxytrityl)-2-deoxy-β-D-lyxofuranosyl)thymine, prepared according to Example 3 |
| 0.72 g | (3.25 mmol) | p-nitrophenylsulfonyl chloride (nosyl chloride) |
| 15 ml | | pyridine (anhydrous) |

Procedure: In a 25-ml one-necked flask with gas connection, the 1-(5-O-(4,4'-dimethoxytrityl)-2-deoxy-β-D-lyxofuranosyl)thymine and nosyl chloride are introduced into anhydrous pyridine at room temperature under inert gas and stirring, then are stirred for 6 days. In the subsequent TLC control test (V(MeOH):V(CH$_2$Cl$_2$)=1:19), only a faint spot corresponding to the starting material (R$_f$=0.31) is still visible. About 3 g of silica gel 60 is added to the brown reaction solution, and the pyridine is removed by means of the rotary evaporator at first and then by high vacuum for 16 hours. The product is isolated by means of column chromatography (silica gel 60; Ø=2.9 cm; h=36 cm; V(MeOH):V(CH$_2$Cl$_2$)=1:19+0.1% of triethylamine).

| Yield: | 0.48 g | (0.66 mmol) | 61.7% of theoretical |
|---|---|---|---|
| Properties: | pale-yellow, amorphous solid; m.p. = 85.9 to 93.4° C.; R$_f$ = 0.53 (V(MeOH):V(CH$_2$Cl$_2$) = 1:19) | | |

2. Synthesis of the Product Compound

| Starting mixture: | | |
|---|---|---|
| 0.57 g | (0.78 mmol) | 1-(5-O-(4,4'-dimethoxytrityl)-3-O-nosyl-2-deoxy-β-D-lyxofuranosyl)thymine |
| 0.51 g | (2.34 mmol, 0.54 ml) | pyrocarbonic acid di-tert-butyl ester (Boc$_2$O) |
| 15 ml | | pyridine (anhydrous) |

Procedure: In a 25-ml one-necked flask with gas connection, 1-(5-O-(4,4'-dimethoxytrityl)-3-O-nosyl-2-deoxy-β-D-lyxofuranosyl)thymine is placed in anhydrous pyridine at room temperature under inert gas and stirring, then Boc$_2$O is added dropwise. After 2.5 days, a product spot (R$_f$=0.62) is visible instead of the spot corresponding to starting material (R$_f$=0.19) in the TLC control test (V(Et$_2$O)=100%). To the orange-brown reaction solution there is added 3 g of silica gel 60, and the solvent is removed by means of the rotary evaporator at first and then by high vacuum for 16 hours. The product is isolated by column chromatography (silica gel 60; Ø=2.9 cm; h=33 cm; V(Et$_2$O)=100+0.1% of triethylamine).

| Yield: | 0.38 g | (0.46 mmol) | 58.9% of theoretical |
|---|---|---|---|
| Properties: | pale-yellow, amorphous solid; m.p. = 118.8 to 120.6° C.; R$_f$ = 0.62 (V(Et$_2$O) = 100%) | | |

EXAMPLE 6

Synthesis of 3'-[$^{18}$F]fluoro-3'-deoxythymidine ([$^{18}$F]FLT)

| Starting mixture: | | |
|---|---|---|
| | (0.013 mmol) | Labeling precursor according to Examples 1 to 5 |
| 7.8 mg | (0.021 mmol) | Kryptofix ®222 (macrocyclic neutral ligand of Merck for the synthesis) |
| 2.3 ml | | acetonitrile (anhydrous; for the DNA synthesis) |
| 0.15 ml | | 1 M hydrochloric acid |
| 0.15 ml | | 1 M sodium hydroxide solution |

| Starting mixture: | | |
|---|---|---|
| 0.2 ml | (0.020 mmol K$^+$) | 0.05 M potassium carbonate (aq) |
| 15392 MBq | (416 mCi) | [$^{18}$F]fluoride at time T$_0$ |

Procedure: The synthesis takes place in the system described hereinafter and shown in FIG. 1. To ensure radiological protection, this system is contained in a lead castle. All necessary manipulations and the HPLC can be controlled from outside. Double 6-way motorized valve D is turned on synchronously at the appropriate positions. Thus the transport paths for solutions and gases are ensured.

The respective reagent can be transferred from one of the receivers A via 6-way motorized valve B and through line a into programmable motorized syringe C. After an intermediate step for pressure equalization inside the syringe, the reagent is transported through line b and double 6-way motorized valve D (position 1) into reactor E, which is positioned in a heating bath (not shown). Pressure equalization inside the reactor takes place via line c, which leads via valve D (position 1) to a pressure-equalization vessel F. Venting of F takes place via an aluminum oxide cartridge, which prevents contamination of the environment with hydrogen [$^{18}$F]fluoride or a contaminated aerosol. Each transport step, for example from a receiver into the reactor, is repeated one time in order to remove solvent residues from the capillaries.

Azeotropic drying of the Kryptofix®/potassium [$^{18}$F] fluoride complex is performed in position 6 of valve D. For this purpose, the he inert-gas stream is passed into reactor E through the boiling reaction solution, and the azeotrope is transferred via line c into cold trap G. The cold trap is also vented via an aluminum oxide cartridge.

To begin the synthesis or hydrolysis, valve D is moved to position 2 during the heatup phase of the reaction solution. This permits pressure equalization of reactor gas space E via capillaries c and cold trap G, which is stabilized at room temperature with water. Position 3 of valve D closes the reactor gas-tightly and permits reaction temperatures above the boiling point of the solvent. Because of the pressure rise inside reactor E, as much as 30% of the reaction mixture—depending on the volume of solvent—is forced into capillaries b, which extend to the reactor bottom. By briefly lowering the reaction temperature below the boiling point of the solvent, the reaction mixture is transferred from the capillaries back into the reactor. After cooling of the reaction vessel at the end of synthesis or hydrolysis, pressure equalization takes place in position 5 of valve D.

To complete the synthesis, the reaction solution is drawn from reactor E via valve D (position 1) into motorized syringe C and from there via valve B (position 6) selectively into a lead-shielded product vial H, or is dispensed to HPLC loop J. After preparative separation, the pure product is fractionated into product vials in a collection station, while the other fractions are separated into a waste vessel.

For synthesis of [$^{18}$F]FLT, the reactor is filled with a solution of Kryptofix® in 1 ml of anhydrous acetonitrile, receiver 2 is filled with 1 ml of acetonitrile for azeotropic drying, receiver 3 is filled with a solution of the labeling precursor in 300 µl of anhydrous acetonitrile, and receivers 4 and 5 are each filled with 150 µl of 1 M hydrochloric acid for hydrolysis or 1 M sodium hydroxide solution for neutralization of the reaction solution. A lead-shielded conical-bottom vial with septum and aeration cannula is filled with the [$^{18}$F]fluoride-containing aqueous potassium carbonate solution and attached to the apparatus as lead-shielded receiver 1, after the activity $A_{OA}$ at time $T_0$ has been determined. In the first step, the basic [$^{18}$F]fluoride solution is transferred into the reactor, after which the residual activity in the conical-bottom vial is determined and the azeotrope present in the reactor is distilled off in the helium stream at a heating-bath temperature of t≈115° C. Approximately 14 minutes after $T_0$, the internal temperature of the reactor reaches t≧110° C. After 2 minutes the reactor is allowed to cool to t≦90° C. and then filled with 1 ml of acetonitrile, after which the azeotropic drying step is repeated. About 1 minute after the internal temperature of the reactor has again reached t≧110° C., the reactor is allowed to cool to t≦75° C., and the solution of labeling precursor in acetonitrile is transferred into the reactor. About 28 minutes after $T_0$, the synthesis of the [$^{18}$F]fluorine-labeled intermediate begins. The synthesis time amounts to 10 minutes at a heating-bath temperature of t≈115° C. with the reactor sealed. After the temperature of the reaction solution has exceeded t=105° C.—which takes place about 3 minutes after the beginning of synthesis—the internal temperature of the reactor is allowed to drop to t≦80° C. within 3 minutes, after which the reactor is reheated to t≈110° C. until the end of the synthesis time. After the reaction solution has cooled to t≦75° C., hydrochloric acid solution is added thereto. Approximately 42 minutes after $T_0$, hydrolysis of the labeled intermediate to [$^{18}$F]FLT begins, the working steps of the synthesis of the intermediate being repeated for this purpose. The orange-brown, faintly reaction cloudy solution cooled to t≦75° C. is neutralized with sodium hydroxide solution, stirred for about 20 seconds and transferred into the HPLC injection loop. The start of the HPLC run takes place about 58 minutes after $T_0$. The [$^{18}$F]FLT is eluted in high purity (HPLC column: Phenomenex; LUNA; 5 μm; 21×250 mm; isocratic; 10 m/min) at a retention time of about $T_R$≈34 to 41 minutes in an aqueous ethanolic solution (V(EtOH):V(H$_2$O)=7.5:92.5).

| Yield: | | |
|---|---|---|
| 1106 MBq | (29.9 mCi) | 9.3% of theoretical; uncorrected measured at time T = 97:20 minutes after $T_0$ |
| 2042 MBq | (55.2 mCi) | 17.2% of theoretical: corrected to time $T_0$; |

The percentage yield is relative to an initial activity of $A_0$=11892 MBq, which is obtained by subtracting, from the initial activity $A_{OA}$=15392 MBq described in the starting mixture, the residual activity of $A_{OR}$=1228 MBq remaining in the conical-bottom vial and the activity loss, corrected to $T_0$, of $A_{OK}$=2272 MBq in the cold trap. It is necessary to take $A_{OK}$ into consideration only if the activity in the cold trap at the end of the synthesis is abnormally high. One cause of such activity can be, for example, a blockage in the exhaust-air system of the apparatus and the resulting boiling delays during azeotropic drying.

Properties: colorless, clear, ethanolic aqueous solution; pH 5.5; free of [$^{18}$F]fluoride; specific activity: 33 MBq/ml (0.88 mCi/ml).

What we claim is:

1. A compound of formula (1)

in which
R denotes triphenylmethyl substituted in the phenyl group, or triphenylsilyl, substituted in the phenyl group,
R' denotes R$^1$—SO$_2$, where R$^1$ is an unsubstituted or substituted C$_1$ to C$_5$ alkyl or an unsubstituted or substituted phenyl, and
R" denotes C$_2$ to C$_{10}$ alkyloxycarbonyl.

2. A compound according to claim 1, wherein the substituent on the phenyl group is chosen from among methyl, ethyl, methoxy and ethoxy.

3. A compound according to claim 1, wherein R denotes 4,4'-dimethoxytriphenylmethyl.

4. A compound according to claim 1, wherein R$^1$—SO$_2$ denotes methanesulfonyl, 4-nitrophenylsulfonyl, p-toluenesulfonyl or trifluoromethanesulfonyl.

5. A compound according to claim 1, wherein the C$_2$ to C$_{10}$ alkyloxycarbonyl is tert-butoxycarbonyl or neopentoxycarbonyl.

6. A compound according to claim 1, wherein the compound is selected from the group consisting of 3-N-Boc-1-(5-O-(4,4'-dimethoxytrityl)-3-O-nosyl-2-deoxy-β-D-lyxofuranosyl)thymine, 3-N-Boc-1-(5-O-(4,4'-dimethoxytrityl)-3-O-tosyl-2-deoxy-β-D-lyxofuranosyl)thymine and 3-N-Boc-1-(5-O-(4,4'-dimethoxytrityl)-3-O-mesyl-2-deoxy-β-D-lyxofuranosyl)thymine.

7. A method for preparation of a compound of formula (1)

in which
R denotes triphenylmethyl substituted in the phenyl group or triphenylsilyl substituted in the phenyl group,
R' denotes R$^1$—SO$_2$, where R$^1$ is an unsubstituted or substituted C$_1$ to C$_5$ alkyl or an unsubstituted or substituted phenyl, and
R" denotes C$_2$ to C$_{10}$ alkyloxycarbonyl, the method comprising reacting a compound of formula (2)

(2)

in which

R denotes triphenylmethyl substituted in the phenyl group, or triphenylsilyl substituted in the phenyl group, and R' denotes $R^1$—$SO_2$, where $R^1$ is an unsubstituted or substituted $C_1$ to $C_5$ alkyl or an unsubstituted or substituted phenyl, with pyrocarbonic acid di-$C_2$–$C_{10}$ alkyl esters.

8. A method according to claim 7, wherein the compound of formula (2) is obtained by reacting the compound of formula (3)

(3)

with $R^1$—$SO_2$Hal, where $R^1$ is an unsubstituted or substituted $C_1$ to $C_5$ alkyl or an unsubstituted or substituted phenyl and Hal denotes a halogen, whereby the substituent R' is introduced.

9. A method according to claim 8, wherein the compound of formula (3) is prepared from thymidine by introduction of the substituent R and inversion.

10. A method for synthesizing 3'-[$^{18}$F]fluoro-3'-deoxythymidine, the method comprising reacting a compound with a formula:

(1)

in which

R denotes triphenylmethyl substituted in the phenyl group, or triphenylsilyl substituted in the phenyl group, R' denotes $R^1$—$SO_2$, where $R^1$ is an unsubstituted or substituted $C_1$ to $C_5$ alkyl or an unsubstituted or substituted phenyl, and R" denotes $C_2$ to $C_{10}$ alkyloxycarbonyl, with a composition to substitute the OR' group by $^{18}$F.

11. The method according to claim 10 further comprising removing the protecting groups R" and R.

* * * * *